US012611196B2

(12) United States Patent
Xie et al.

(10) Patent No.: US 12,611,196 B2
(45) Date of Patent: Apr. 28, 2026

(54) ULTRASONIC QUANTIFICATION OF ACOUSTIC ATTENUATION COEFFICIENT IN THE PRESENCE OF ELEVATION APERTURE BLOCKAGE

(71) Applicant: KONINKLIJKE PHILIPS N.V., Eindhoven (NL)

(72) Inventors: Hua Xie, Cambridge, MA (US); Man Nguyen, Melrose, MA (US); Jean-Luc Francois-Marie Robert, Cambridge, MA (US); William Tao Shi, Wakefield, MA (US); Claudia Errico, Medford, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 21 days.

(21) Appl. No.: 18/574,194

(22) PCT Filed: Jun. 20, 2022

(86) PCT No.: PCT/EP2022/066678
§ 371 (c)(1),
(2) Date: Dec. 26, 2023

(87) PCT Pub. No.: WO2023/274763
PCT Pub. Date: Jan. 5, 2023

(65) Prior Publication Data
US 2024/0315674 A1    Sep. 26, 2024

Related U.S. Application Data

(60) Provisional application No. 63/216,133, filed on Jun. 29, 2021.

(51) Int. Cl.
*A61B 8/00*     (2006.01)
*G01S 7/52*     (2006.01)
*G01S 15/89*    (2006.01)

(52) U.S. Cl.
CPC ............ *A61B 8/5269* (2013.01); *A61B 8/461* (2013.01); *A61B 8/488* (2013.01); *A61B 8/54* (2013.01);
(Continued)

(58) Field of Classification Search
None
See application file for complete search history.

(56) References Cited

U.S. PATENT DOCUMENTS 4,441,368 A * 4/1984 Flax ........................ G01H 3/00
                                                      73/599
5,833,613 A   11/1998 Averkiou et al.
(Continued)

FOREIGN PATENT DOCUMENTS

WO    2015087218 A1    6/2015
WO    2021018968 A1    2/2021

OTHER PUBLICATIONS

Y. Labyed et al, "A theoretical comparison of attenuation measurement techniques from backscattered ultrasound echoes", Journal of the Acoustical Society of America, vol. 129, No. 4, pp. 2316-2324, May 2010 (Year: 2010).*
(Continued)

*Primary Examiner* — Nyrobi Celestine

(57) ABSTRACT

An ultrasonic diagnostic imaging system and method produce attenuation coefficient maps of a region of interest in an ultrasound image. In order to detect the presence of elevation aperture blockage, the system estimates attenuation coefficients by two different methods. The estimates produced by the two different methods are combined to produce a metric, which is evaluated as a function of depth. If the metric satisfies one or more criteria of measurement bias, elevation aperture blockage is identified and an alert of the blockage is produced for the user.

18 Claims, 9 Drawing Sheets

(52) U.S. Cl.
CPC ...... *G01S 7/52036* (2013.01); *G01S 7/52053* (2013.01); *G01S 15/8915* (2013.01); *G01S 15/8979* (2013.01)

(56) References Cited

U.S. PATENT DOCUMENTS

| | | | | |
|---|---|---|---|---|
| 2007/0238991 A1* | 10/2007 | Amararene | .............. | A61B 8/00 |
| | | | | 600/442 |
| 2010/0069753 A1* | 3/2010 | Fedewa | .................. | A61N 7/022 |
| | | | | 600/439 |
| 2018/0122107 A1* | 5/2018 | Li | .......................... | G06T 11/005 |
| 2020/0256971 A1* | 8/2020 | Huang | ................. | A61B 8/5269 |
| 2021/0022710 A1* | 1/2021 | Crocco | .............. | G01S 15/8915 |
| 2022/0087653 A1* | 3/2022 | Huang | ............... | G01S 7/52036 |
| 2022/0280138 A1* | 9/2022 | Huang | ................. | A61B 8/5269 |

OTHER PUBLICATIONS

International Search Report and Written Opinion for PCT/EP2022/066678; Mailing date: Sep. 28, 2022, 10 pages.

Kim, H. et al., "Hybrid Spectral Domain Method for Attenuation Slope Estimation", Ultrasound in Medicine & Biology, 2008, vol. 34, Issue 11, pp. 1808-1819.

Omari, E. et al., "Evaluation of the impact of backscatter intensity variations on ultrasound attenuation estimation", Med. Phys., 2013, vol. 40, Issue 8, 10 pages.

Samimi, K. et al., "Optimum Diffraction-Corrected Frequency-Shift Estimator of the Ultrasonic Attenuation Coefficient", IEEE Transactions on Ultrasonics, Ferroelectrics, and Frequency Control, 2016, vol. 63, No. 5, pp. 691-702.

Klimonda, Z. et al., "Tissue Attenuation Estimation by Mean Frequency Downshift and Bandwidth Limitation", IEEE Transactions on Ultrasonics, Ferroelectrics, and Frequency Control, 2016, vol. 63, No. 8, pp. 1107-1115.

* cited by examiner 1.5 dB/cm/MHz 0 dB/cm/MHz

1

ULTRASONIC QUANTIFICATION OF ACOUSTIC ATTENUATION COEFFICIENT IN THE PRESENCE OF ELEVATION APERTURE BLOCKAGE

CROSS-REFERENCE TO PRIOR APPLICATIONS

This application is the U.S. National Phase application under 35 U.S.C. § 371 of International Application No. PCT/EP2022/066678, filed on Jun. 20, 2022, which claims the benefit of U.S. Provisional Patent Application No. 63/216,133, filed on Jun. 29, 2021. These applications are hereby incorporated by reference herein.

This invention relates to medical diagnostic ultrasound systems and, in particular, to ultrasound systems which produce quantified measurements of the acoustic attenuation of tissue to the passage of ultrasound.

One of the long-sought objectives of medical diagnostic ultrasound is tissue characterization, the ability to determine noninvasively with ultrasound whether in situ tissue is malignant or benign. Efforts directed toward tissue characterization have generally involved trying to quantitatively measure the interaction of tissue with ultrasonic energy as evidenced by characteristics of returning echo signals. One such effort is acoustic attenuation measurement which tries to quantify the resistance of tissue to the passage of ultrasound. Acoustic attenuation is measured by the energy loss of sound propagation along the propagation path in media. It plays an important role in tissue characterization as it is a tissue-specific physical parameter. Acoustic attenuation also changes as a function of tissue pathology, composition and therapeutic treatment. Because of this property, acoustic attenuation has been explored as a quantifiable tissue parameter for tissue characterization and diagnosis. Since fat is more attenuative than normal liver tissue, acoustic attenuation coefficient assessment can potentially be used to quantify the fat accumulated inside liver cells and subsequently stage fatty liver disease. The widespread occurrence of non-alcoholic fatty liver disease and non-alcoholic steato-hepatitis has spurred fundamental research, clinical validation and commercialization for quantification of acoustic attenuation using ultrasound. Compared to the gold standard of liver biopsy and the reference diagnostic standard of MRI proton density fat fraction assessment, ultrasound pulse-echo mode-based methods offer non-invasive, real-time and cost-effective advantages for liver steatosis assessment, and are therefore more suitable for general population screening and frequent follow-up for treatment monitoring.

When clinical decision-making is based on a diagnostic quantified measurement, it is important that the measurements be made accurately so that clinical decisions are not based on inaccurate data. In ultrasound this means eliminating extraneous effects and variables from measurements. One such source of extraneous effects is the effect of ultrasound system operating and control parameters on the production of the system's acoustic echo data. These effects are generally quantified and eliminated as a possible error source to acoustic quantification by modelling the effects of system operation and taking them into consideration in the final production of acoustic data, or by measuring echo data produced by a system from a phantom of known properties and accounting for variances in the final production of data. Other effects which must be taken into consideration are aberration effects of anatomy in the body, such as subcutaneous layers of fat which can alter the speed of sound from that which is otherwise expected in the underlying tissue, and can cause variation in beamforming and other operations which rely upon accurate time-of-flight measurement.

A third category of data inaccuracy are assumptions of data processing algorithms and circuitry as to the character of the transmission of acoustic energy into the body and its complete return in echo signals. One such problem of this sort is addressed by an implementation of the present invention, the problem of effects on the transmission and reception of acoustic energy which arise when trying to diagnose underlying organs and tissue when aiming ultrasound between the ribs. Two organs which can present this problem are the liver and the heart, where frequently the sonographer is forced to use an acoustic aperture between two ribs to access the organ of interest. The sonographer may assume when using a rib aperture that the production of a good quality ultrasound image means that the probe is properly positioned between the ribs. However, the present inventors have found that a particular problem may arise when trying to make acoustic attenuation measurements through an intercostal space. Even though the azimuth aperture of the probe is properly aligned with the rib spacing, some blockage of beam transmission in the elevation direction may occur. This blockage will cause an alteration of the acoustic energy pattern transmitted and received from that upon which standard attenuation measurement algorithms are based. The result is an overestimation or underestimation bias in acoustic attenuation quantification by the standard algorithms and hence an inaccurate mapping of acoustic attenuation in the anatomy of interest, complicating and compromising clinical decision-making.

In accordance with the principles of the present invention, a diagnostic ultrasound system is described which is able to detect blockage of the elevation aperture when making acoustic attenuation measurements through a rib or other problematic anatomical acoustic aperture. This is done by estimating acoustic attenuation in a region of interest by use of two different acoustic attenuation estimation methods, producing a metric from the two results, then evaluating one or more criteria based on the metric. When the criteria are satisfied, a blockage of the elevation aperture is indicated and the sonographer is alerted to the problem. The ultrasound system may additionally be conditioned to present suggestions to the sonographer on ways to ameliorate the situation, such as tilting or repositioning the probe at the intercostal space.

Figure 1:
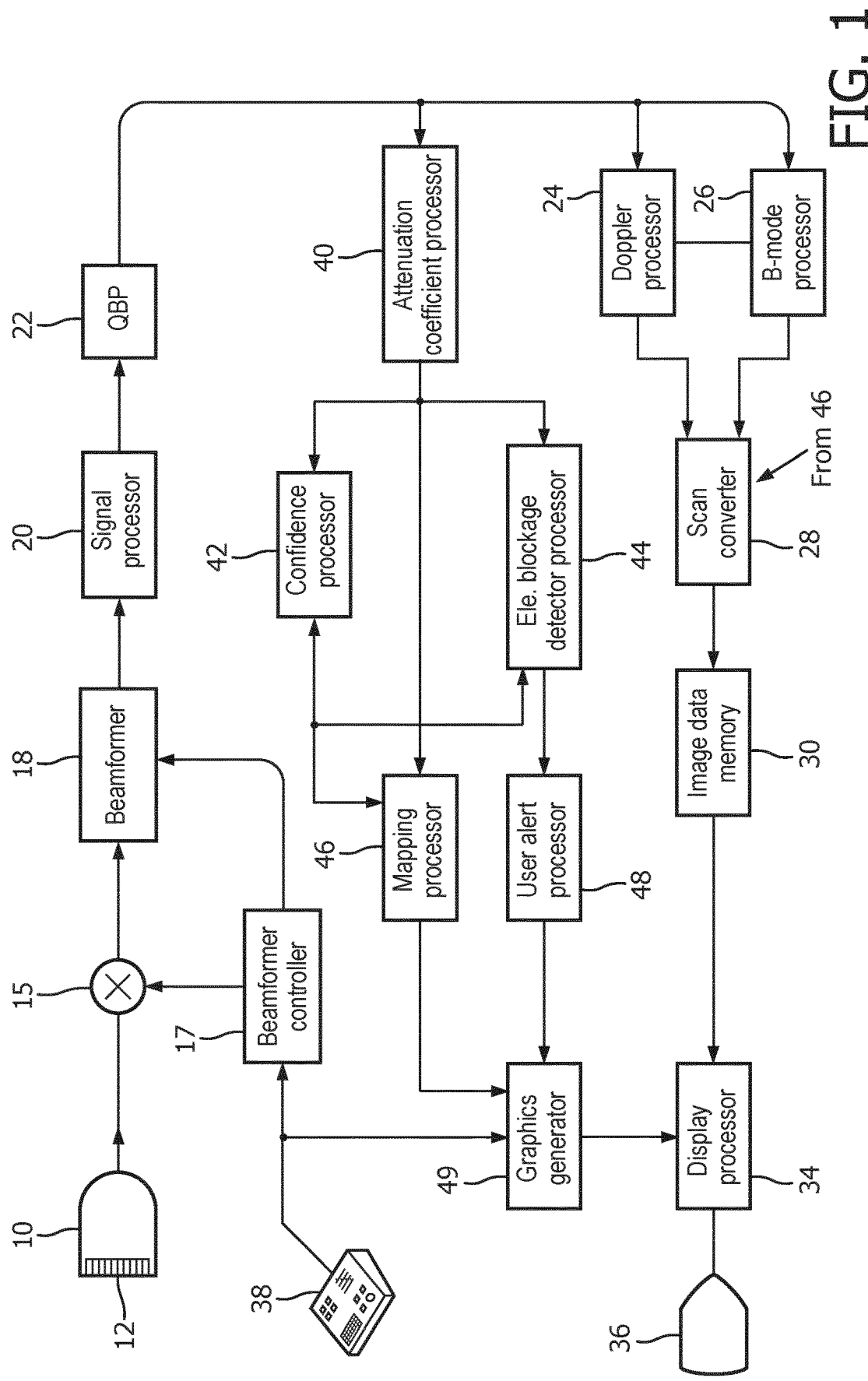
FIG. 1 illustrates in block diagram form an ultrasonic diagnostic imaging system constructed in accordance with the principles of the present invention.

When an acoustic wave travels in soft tissue, acoustic intensity decreases due to absorption and scattering as function of propagation distance and the tissue attenuation coefficient $\alpha(f)$ (in the unit of dB/cm) which is frequency dependent. In one-way propagation, the acoustic intensity $I(f,z)$ at a given position z can be expressed with respect to the acoustic intensity at the origin $z_0$ as $$I(f, z) = I(f, z_0)e^{-2\alpha(f)(z-z_0)} \tag{1}$$

where $$\alpha(f) = \alpha_0 f^n \tag{2}$$

Here $\alpha_0$ is the acoustic attenuation coefficient slope in the units of dB/cm/MHz in the log scale. For low frequencies, a linear or almost linear relationship with frequency is assumed, i.e., n=1 between $\alpha$ and $\alpha_0$.

In two-way pulse-echo mode, the backscattered ultrasound signal is the function of tissue property (i.e., attenuation and backscattering) and system imaging settings of the transducer and scanner. Its power spectrum can be generalized by the following expression as a function of f and z. Estimation of $\alpha$ or $\alpha_0$ from pulse echoes is often based on Equation (3):

$$I_s(f, z) = P(f)D_s(f, z)A_s(f, z_0)B_s(f, z)\exp[-4\alpha_s(f)(z-z_0)] \tag{3}$$

where the subscript s denotes (tissue) sample, f frequency, z depth in the pulse-echo mode, $I(f,z)$ a measured power spectrum from a region of interest (ROI) centered at z, $P(f)$ the transducer response combined with the spectrum of the transmitted pulses, $D(f,z)$ the diffraction effects (including the two-way beam pattern), $z_0$ the starting depth of the ROI, $A(f,z_0)$ the cumulative attenuation effects from the transducer surface to $z_0$, and $B(f,z)$ the effects of tissue backscattering.

As illustrated by Equation (3), the observed acoustic signal intensity at a raw RF (radio frequency) or I, Q (in-phase and quadrature) data level presents more complex spatial profiles than the linear attenuation trend in Equation (1). The signal intensity variation depends not only on the tissue-specific attenuation coefficient but also on several system factors including the two-way transmit/receive beam pattern, transducer lens effects, internal gain such as TGC (time gain compensation) and analog gains, and other beamforming operations. These system-dependent effects must be removed from the signal profile in order to reconstruct the acoustic attenuation coefficient for the tissue under investigation.

Over the last two decades two main calibration approaches have been developed to correct for system dependence. The first is called the reference-phantom based method. It relies on a physical phantom with uniform backscattering strength and known acoustic attention coefficient. The system dependence induced signal change as a function of depth will be estimated from the data acquired on such a phantom and subsequently removed from the tissue signal sample under examination. It is indispensable to maintain the exact acoustic settings between an in vivo scan and the phantom scan by which a reference library is established. If the system acquisition settings undergo significant changes, new measurements on the reference phantom must be performed to update the reference library. The second calibration method is called the modelling-based simulation method. In this method, the entire system signal path from transducer transmission to the summed RF/I, Q signal is simulated.

In the early days of quantitative ultrasound, academic researchers adopted the first approach as they did not have full access to system-level information for both the scanner and the transducer. Even though manufacturers purportedly know every detail in the entire system acoustic design and signal path, it still requires superior expertise in acoustic physics, system signal path design, ultrasound modelling and transducer acoustic measurement to faithfully model an ultrasound system signal path. Because of such high requirements for modelling, physical phantoms are still preferred to system modelling for system calibration for acoustic attenuation imaging.

For insonification of a homogeneous reference phantom (physical or simulated) with a known acoustic attenuation coefficient, the power spectrum of ultrasound signals can be expressed as $$I_r(f, z) = P(f)D_r(f, z)A_r(f, z_0)B_r(f, z)\exp[-4\alpha_r(f)(z-z_0)] \tag{4}$$

where the subscript r denotes the reference phantom.

If we take the ratio of Equation (3) to Equation (4), system factors $P(f)$ and $D(f,z)$ (assuming equal speed of sound) can be suppressed. It is also valid to further assume $B_r(f,z)=B_r(f)$ since the reference phantom has a spatially uniform backscattering coefficient. Then the power spectrum ratio of the tissue signal to the reference signal SR(f,z) is simplified to $$SR(f, z) \equiv \frac{I_s(f, z)}{I_r(f, z)} \cong \frac{A_s(f, z_0)B_s(f, z)}{A_r(f, z_0)B_r(f)}\exp\{-4(z-z_0)[\alpha_s(f) - \alpha_r(f)]\} \tag{5}$$

After removing the system dependence, either of two standard algorithmic methods can be applied to Equation (5) to empirically estimate the acoustic attenuation coefficient $\alpha_s(f)$. Below the methodology of the spectral intensity difference and spectral frequency shift methods is explained.

The spectral intensity difference method can be used to estimate the acoustic attenuation coefficient from (assuming $B_s(f,z)=B_s(f)$)

$$\ln\left[\frac{I_s(f, z_2)}{I_r(f, z_2)}\right] - \ln\left[\frac{I_s(f, z_1)}{I_r(f, z_1)}\right] \cong -4(z_2 - z_1)[\alpha_{0s} - \alpha_{0r}]f + \ln[c] \tag{6}$$

5 where $$\alpha_{0s}(z) = \alpha_{0r} - \frac{1}{4}\frac{\partial}{\partial z}\ln\left[\frac{I_s(f,z)}{I_r(f,z)}\right] = \alpha_{0r} - \frac{1}{4}\frac{\partial}{\partial z}\ln[SR(f,z)] \qquad (7)$$

If it is assumed that n=1, then $\alpha_{0s}$ can be simply recovered from the linear least-square fitting of the slope of $\ln[SR(f,z)]$ over the depth range of the ROI in Equation (7).

The spectral frequency shift method estimates the acoustic attenuation coefficient as follows. Given a Gaussian enveloped transmit pulse P(f) centered at frequency $f_t$ with a power spectrum variance $\sigma_t^2$, and that the spectrum remains Gaussian-shaped during pulse propagation in attenuative soft tissue, the center frequency $f_p$ of the backscattered signal will downshift toward lower frequencies as a function of depth in accordance with Equation (8):

$$f_p(z) = f_t - 4(\alpha_{0s} - \alpha_{0r})z\sigma_t^2 \qquad (8)$$

where $$\alpha_{0s}(z) = \alpha_{0r} - \frac{1}{4\sigma_t^2}\frac{\partial}{\partial z}(f_p(z)) \qquad (9)$$

To remove the diffraction effect, SR(f,z) is first derived and then shaped in a passband by applying a Gaussian-like weighting function $$\exp\left(-\frac{(f-f_t)^2}{2\sigma_t^2}\right).$$

For a Gaussian spectrum, the peak (or center) frequency can be estimated from the centroid frequency with correction due to a bandwidth-limited spectrum; or by direct Gaussian function fitting. Finally, the acoustic attenuation coefficient of the tissue can be calculated from the derivative of the center frequency with respect to depth as indicated in Equation (9).

These two acoustic attenuation coefficient estimation methods have pros and cons for in vivo acoustic attenuation quantification. The spectral intensity difference method does not assume any spectrum characteristics, therefore it is less strict as to the transmitted pulse type. However, this method is prone to estimation error if the tissue in the ROI exhibits spatial discontinuity in backscattering coefficient (e.g., dark vessels or hypoechoic or hyperechoic focal lesions in liver tissue). On the other hand, the spectral frequency shift method is more robust to spatial variation of backscattering, but it will break down if the assumption of a Gaussian-shaped transmit pulse becomes invalid. As a consequence, hybrid approaches have been proposed which involve elements of both methods. See, e.g., "Hybrid Spectral Domain Method for Attenuation Slope Estimation," by H. Kim et al., *Ult. In Medicine and Biol.*, vol. 34, no. 11 at pp 1808-1819 (2008).

An ultrasound system which uses both the spectral intensity method and the spectral frequency shift method to estimate the acoustic attenuation coefficient and consequently to detect the presence of elevation aperture blockage in accordance with the principles of the present invention is illustrated in FIG. 1. In the drawing, an ultrasound system constructed in accordance with the principles of the present invention is shown in block diagram form. A transducer array 12 is provided in an ultrasound probe 10 for transmitting ultrasonic waves and receiving echo information. The transducer array 12 in this implementation is a one-dimensional (1D) array of transducer elements capable of scanning an azimuth plane in front of the row of elements by steering and focusing beams in the plane. Being only a single element wide, the array of a 1D transducer probe has no ability to steer or focus beams in the orthogonal elevation direction. However most 1D array probes are constructed with a fixed elevation focus that shapes the transmitted ultrasound in the elevation dimension in a general hourglass shape by the use of a lens or shaping of the transducer elements. The narrowest point of the hourglass shape is the fixed focus in the elevation dimension. Elevation focusing can also be achieved by using a few transducer elements on either side of the center row of elements which are connected to operate in fixed synchrony with the center row to produce fixed elevation focusing by phased transmission, a so-called 1.5D (or 1.xD) array transducer. The elements of the transducer array are coupled by a probe cable to a transmit/receive (T/R) switch 16 which switches between transmission and reception and protects the beamformer 18 from high energy transmit signals. The transmission of ultrasonic beams from the transducer array 12 under control of the beamformer is directed by a beamformer controller 17 coupled to the T/R switch and the beamformer, which receives input from the user's operation of the user interface or control panel 38. Among the transmit characteristics controlled by the controller are the direction, number, spacing, amplitude, phase, frequency, polarity, and diversity of transmit waveforms. Beams formed in the direction of pulse transmission may be steered straight ahead from the transducer array, or at different angles for a wider sector field of view. Beamformers may process echo signals in their received analog form or may digitize signal samples and process the echo signals digitally.

The echoes received by elements of the array are beamformed by the beamformer 18 by appropriately delaying them and then combining them to produce a coherent echo signal. For example, the beamformer 18 may have 128 channels, each of which controls transmission by and delays signals received from a particular element of a 128-element array transducer.

The coherent echo signals undergo signal processing by a signal processor 20, which includes filtering by a digital filter and noise (speckle) reduction as by spatial or frequency compounding. The digital filter of the signal processor 20 can be a filter of the type disclosed in U.S. Pat. No. 5,833,613 (Averkiou et al.), for example. The echo signals are then coupled to a quadrature bandpass filter (QBP) 22. The QBP performs three functions: band limiting the RF echo signal data, producing in-phase and quadrature pairs (I and Q) of echo signal data, and decimating the digital sample rate. The QBP comprises two separate filters, one producing in-phase samples and the other producing quadrature samples, with each filter being formed in a digital implementation by a plurality of multiplier-accumulators (MACs) implementing an FIR filter.

The beamformed and processed coherent echo signals are coupled to a pair of image data processors. A B mode processor 26 produces image data for a B mode image of structure in the body such as tissue. The B mode processor performs amplitude (envelope) detection of quadrature demodulated I and Q signal components by calculating the echo signal amplitude in the form of $(I^2+Q^2)^{1/2}$. The quadrature echo signal components are also coupled to a Doppler processor 24. The Doppler processor 24 stores ensembles of echo signals from discrete points in an image field which are then used to estimate the Doppler shift at points in the image with a fast Fourier transform (FFT) processor. The rate at which the ensembles are acquired determines the velocity range of motion that the system can accurately measure and depict in an image. The Doppler shift is proportional to motion at points in the image field, e.g., blood flow and tissue motion. For color Doppler image data, the estimated Doppler flow values at each point in a blood vessel are wall filtered and converted to color values using a look-up table. The wall filter has an adjustable cutoff frequency above or below which motion will be rejected such as the low frequency motion of the wall of a blood vessel when imaging flowing blood. The B mode image data and the Doppler flow values are coupled to a scan converter 28 which converts the B mode and Doppler samples from their acquired R-θ coordinates to Cartesian (x,y) coordinates for display in a desired display format, e.g., a rectilinear display format or a sector display format. Either the B mode image or the Doppler image may be displayed alone, or the two shown together in anatomical registration in which the color Doppler overlay shows the blood flow in B mode processed tissue and vessels in the image. Another display possibility is to display side-by-side images of the same anatomy which have been processed differently. This display format is useful when comparing images. The scan-converted image data, both B mode and Doppler data, is coupled to and stored in an image data memory 30 where it is stored in memory locations addressable in accordance with the spatial locations from which the image data values were acquired. Two-dimensional images of a plane scanned by the transducer probe are assembled from image data stored in the image data memory and are coupled to a display processor 34 for further enhancement, buffering and temporary storage for display on an image display 36.

In accordance with the present invention, I, Q data produced by the QBP filter 22 is also coupled to an attenuation coefficient processor 40. The attenuation coefficient processor executes the spectral intensity difference and spectral frequency shift algorithms using the phase-sensitive I, Q echo signal data from the QBP filter. For each point in an ROI, the attenuation coefficient processor produces an attenuation coefficient estimate $\alpha_1$ by the spectral intensity difference method, and an attenuation coefficient estimate $\alpha_2$ by the spectral frequency shift method. The attenuation coefficients are coupled to a confidence processor 42, an elevation blockage detector processor 44, and a mapping processor 46. The confidence processor utilizes the attenuation estimates to produce confidence factor values for each point in the ROI, which are forwarded to the mapping processor 46 for the production of a confidence map of the ROI. Confidence factor values for points in an ROI may be determined by a number of known techniques. For instance, for the spectral intensity difference method of attenuation coefficient estimation to be valid for accurate coefficient slope estimation, it is necessary for the following expression $$Q(f, z_1, z_2) \equiv \frac{1}{f}\left(\ln\left[\frac{s_s(f, z_2)}{s_r(f, z_2)}\right] - \ln\left[\frac{s_s(f, z_1)}{s_r(f, z_1)}\right]\right) - 4\beta_r \quad [10]$$

8 to be independent of f. It will be if $$Q(f, z_1, z_2) \cong \bar{Q}(z_1, z_2) \equiv \frac{\int_{f_1}^{f_2} w(f)Q(f, z_1, z_2)df}{\int_{f_1}^{f_2} w(f)df} \quad [11]$$

It can be determined if this is the case by calculating $$u(z_1, z_2) \equiv \frac{\sqrt{\frac{\int_{f_1}^{f_2} w(f)[Q(f, z_1, z_2) - \bar{Q}(z_1, z_2)]^2 df}{\int_{f_1}^{f_2} w(f)df}}}{|\bar{Q}(z_1, z_2)|} \quad [12]$$

The confidence in the attenuation coefficient estimates is greater when u is smaller and lower when u is larger. A map of u values calculated in this manner for each pixel of an attenuation coefficient map calculated by the spectral difference method thus will inform the user of the trustworthiness of the attenuation coefficient map and the accuracy of coefficient estimations for the points throughout the attenuation coefficient map.

Confidence factor values are also coupled to the elevation blockage detector processor 44. The mapping processor 46 also receives attenuation coefficient values for each point in the ROI for the assembly of an attenuation coefficient map of the ROI. The elevation blockage detector processor receives attenuation coefficient estimates produced by both methods and confidence factor values for each point in the ROI for the possible detection of elevation blockage, as more fully described below. If elevation blockage is detected, a signal is sent to the user alert processor 48 for the production of an alert to the system operator of the detected condition. Maps produced by the mapping processor 46 and user alerts produced by the user alert processor 48 are coupled to a graphics generator 49 for display in conjunction with an ultrasound image by the display processor 34 on the display 36. If the attenuation maps are not produced in the desired display coordinates, e.g., Cartesian rather than radial, the map values may be coupled to the scan converter 28 for coordinate conversion. Another alternative is for the mapping processor 46 to perform the coordinate conversion. The user control panel 38 is also coupled to the graphics generator for the reception and display of alphanumeric data enter by the user on the user control, such as patient name. User alerts may also be reproduced audibly by the ultrasound system's loudspeaker (not shown).

Figure 2:
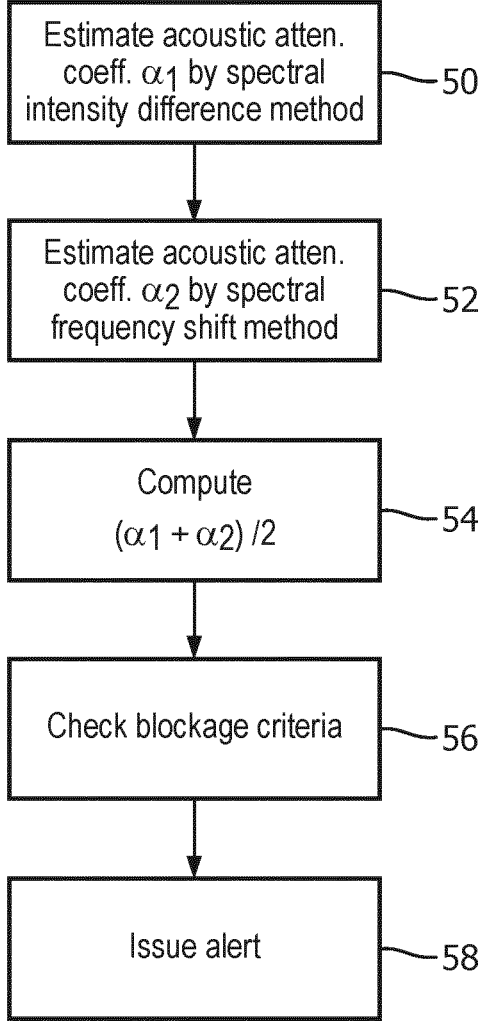
FIG. 2 illustrates a first implementation of the attenuation coefficient processor and elevation blockage detector processor of FIG. 1.

In accordance with a further aspect of the present invention, acoustic attenuation coefficient values produced by the two estimation methods are used by the elevation blockage detector processor 44 to detect elevation aperture blockage in one of several different ways. One way is illustrated by the flow diagram of FIG. 2, which utilizes an average of the two attenuation coefficient estimation techniques. In step 50, an acoustic attenuation coefficient is estimated for a particular point in an ROI by the spectral intensity difference method by the attenuation coefficient processor. In step 52, an acoustic attenuation coefficient is estimated for the same point in an ROI by the spectral frequency shift method by the attenuation coefficient processor. The two estimates $\alpha_1$ and $\alpha_2$ are coupled to the elevation blockage detector processor, where they are used in step 54 to compute an average of the two attenuation coefficient values, $(\alpha_1+\alpha_2)/2$. This combination of the two attenuation coefficient values is used by the elevation blockage detector processor in step 56 to check blockage criteria and thereby detect the presence of elevation blockage, as described in detail below. If a blockage is detected, an alert is issued in step 58.

Figure 3:
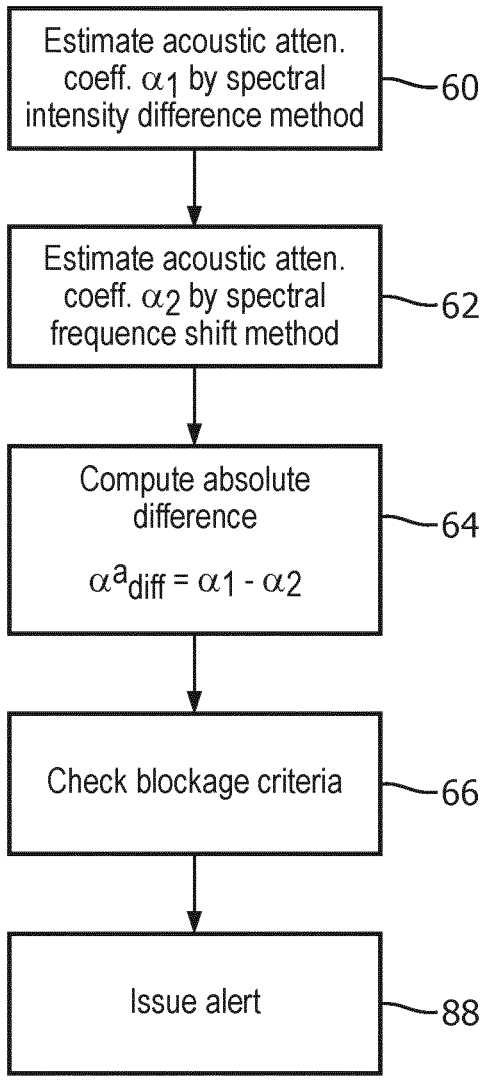
FIG. 3 illustrates a second implementation of the attenuation coefficient processor and elevation blockage detector processor of FIG. 1.

FIG. 3 illustrates a process for detecting the presence of elevation blockage using a different combination of the attenuation coefficient estimates $\alpha_1$ and $\alpha_2$, which is the absolute difference, expressed as $\alpha_{diff}{}^{\alpha}=\alpha_1-\alpha_2$. In step 60, the acoustic attenuation coefficient is estimated for a particular point in an ROI by the spectral intensity difference method by the attenuation coefficient processor. In step 62, the acoustic attenuation coefficient is estimated for the same point by the spectral frequency shift method. The two estimates, $\alpha_1$ and $\alpha_2$ are then used to compute their absolute difference in step 64. The absolute difference value is then used by the elevation blockage detector processor in step 66 to detect the presence of elevation blockage. If a blockage is detected an alert is issued in step 68.

Figure 4:
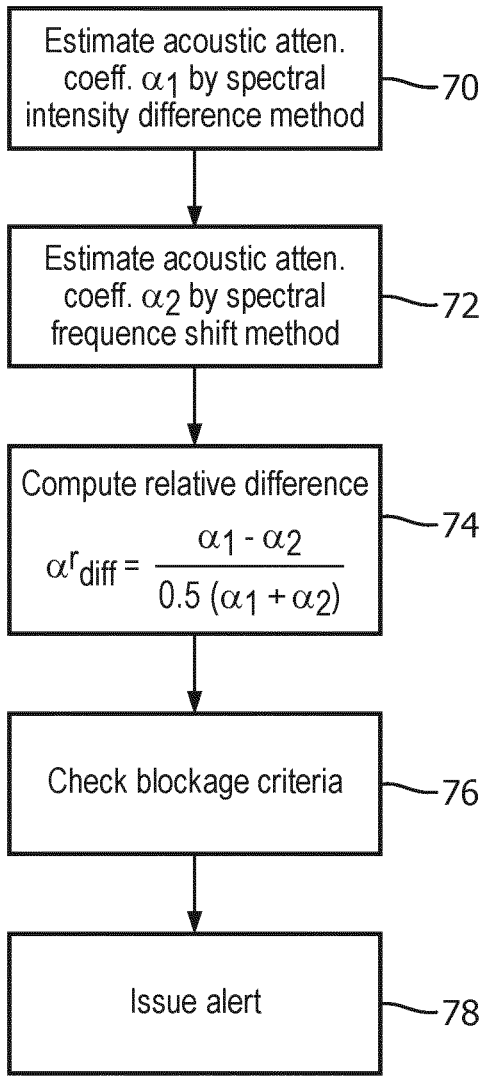
FIG. 4 illustrates a third implementation of the attenuation coefficient processor and elevation blockage detector processor of FIG. 1.

FIG. 4 illustrates a process for detecting the presence of elevation blockage using a third combination of the attenuation coefficient estimates $\alpha_1$ and $\alpha_1$ which is the relative difference, expressed as $$\alpha_{diff}^{r} = \frac{\alpha_1 - \alpha_2}{0.5(\alpha_1 + \alpha_2)}.$$

In Step 70, the acoustic attenuation coefficient is estimated for a particular point in an ROI by the spectral intensity difference method by the attenuation coefficient processor. In step 72, the acoustic attenuation coefficient is estimated for the same point by the spectral frequency shift method. The two estimates $\alpha_1$ and $\alpha_2$ are then used to compute their relative difference in step 74. The relative difference value is then used by the elevation blockage detector processor in step 76 to detect the presence of elevation blockage. If a blockage is detected an alert is issued in step 78.

Figure 5A:
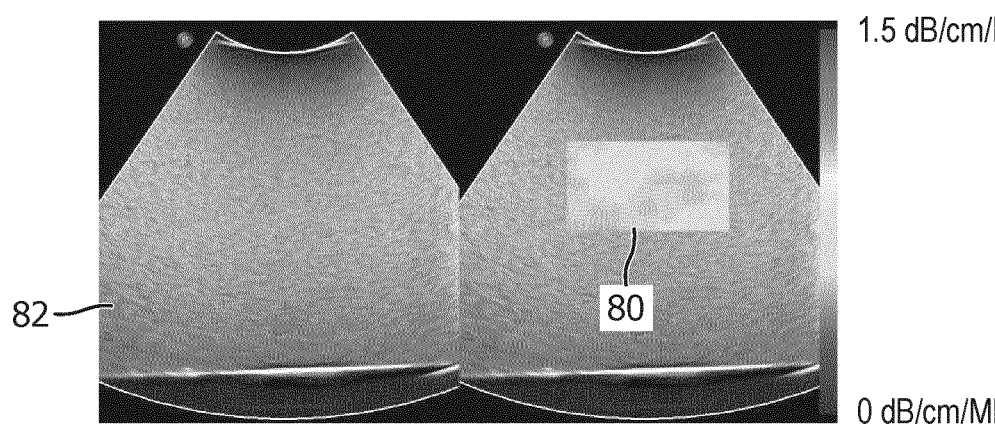
FIGS. 5a-5c illustrate ultrasound images of a phantom with attenuation coefficient maps produced with no elevation aperture blockage, a small amount of blockage, and a large amount of blockage.
Figure 5B:
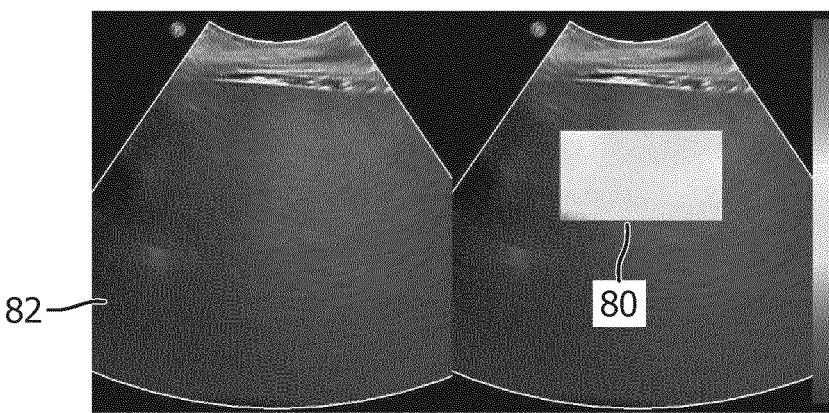
Figure 5C:
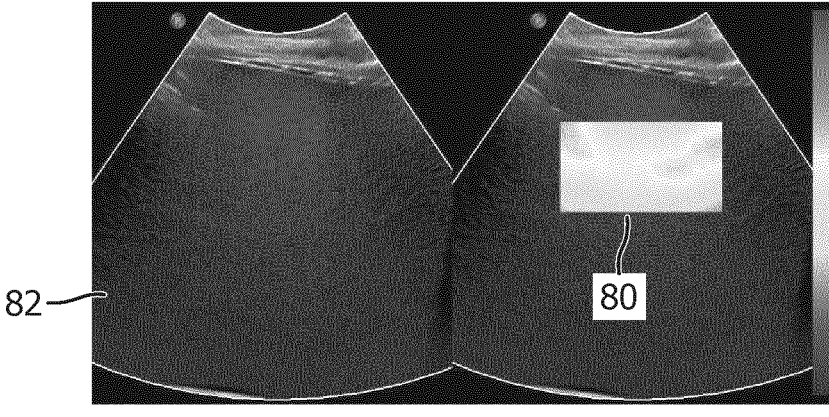

FIGS. 5a-5c illustrate ultrasound images of a phantom which show the effects of elevation aperture blockage. On the left side of each figure is an unrestricted B mode image 82 of the phantom. On the right side of FIG. 5a the phantom is imaged without aperture blockage, and an attenuation coefficient map 80 is calculated for an ROI of the phantom. The attenuation coefficient maps of these illustrations are generated by taking the average of the estimates from the spectral intensity difference method and the spectral shift method and superimposing the maps over the ROI in the image. The attenuation coefficient map of FIG. 5a is seen to be of uniform shading and is consistent with the known attenuation coefficient of the phantom, which is about 0.50 dB/MHz/cm. A piece of porcine tissue containing ribs was then placed on top of the phantom, which is then imaged through the intercostal space of the ribs. FIGS. 5b and 5c present the B-mode image and attenuation map under the influence of two levels of elevation aperture blockage by the ribs. In FIG. 5b the ribs present a relatively low amount of blockage and in FIG. 5c the ribs present a greater amount of blockage. The lighter shading of the attenuation coefficient map in FIG. 5b evidences a low degree of primary overestimation in attenuation, with an averaged attenuation coefficient of ~0.7 dB/MHz/cm. With the greater aperture blockage in FIG. 5c, even greater overestimation of attenuation is evident in the acoustic coefficient map 80, with an averaged attenuation coefficient of ~0.9 dB/MHz/cm. Measurement bias in acoustic attenuation due to overestimation or underestimation of acoustic attenuation will, in the case of liver diagnosis, lead to inaccurate liver fat quantification and compromised diagnostic decision-making.

Figure 6A:
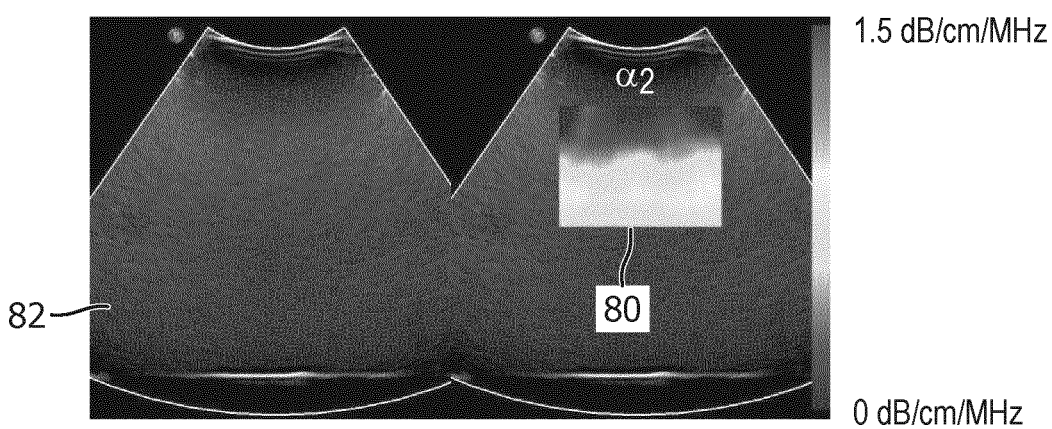
FIGS. 6a-6c illustrate ultrasound images of a phantom with attenuation coefficient maps produced by two different algorithms for attenuation coefficient estimation and by a combination of two estimation methods.
Figure 6B:
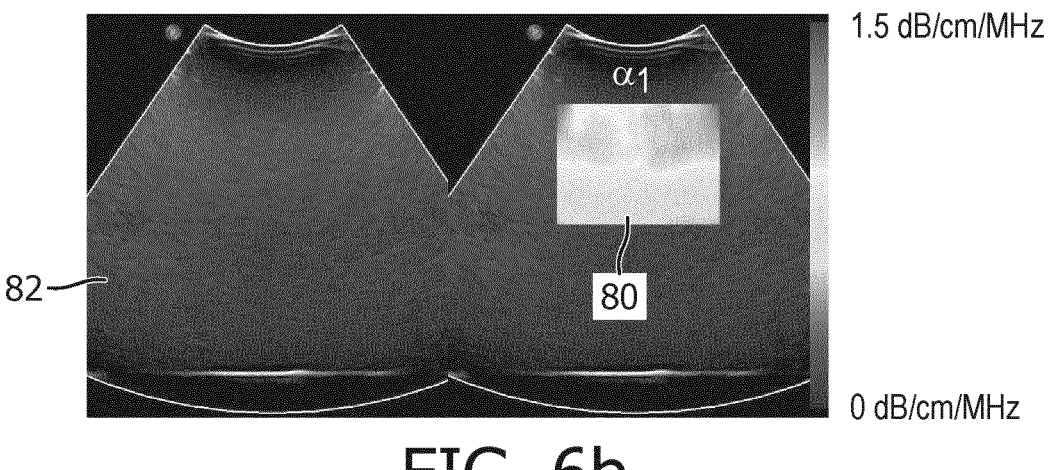

FIGS. 6a and 6b illustrate B mode images with attenuation coefficient maps produced, not by multiple methods of attenuation coefficient estimation, but by the spectral frequency shift method alone and the spectral intensity difference method alone, respectively. For these measurements the phantom with an acoustic attenuation coefficient of 0.50 dB/MHz/cm was used, with 30% blockage of the elevation aperture directly applied to the probe. From the shading of the colorbar on the right side of FIG. 6a, it is seen that the attenuation coefficient map 80 is darkly shaded in the near field with lightly shaded patches in the far field, evidencing an underestimation of attenuation in the near field and an overestimation of attenuation in the far field from the nominal value of 0.50 dB/MHz/cm. In FIG. 6b where attenuation coefficient estimates were produced by the spectral intensity difference method, the shading of the attenuation map 80 evidences significant overestimation in the near field. These attenuation maps may be compared with the attenuation map 80 in FIG. 6c which was produced by averaging estimates produced by the two methods, and evidences only a small degree of overestimation in the midrange of the attenuation map.

Figure 6C:
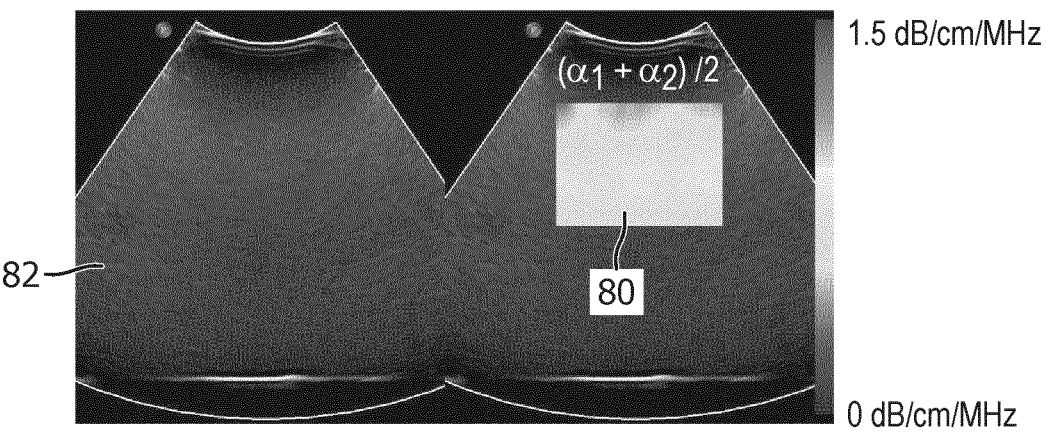

The attenuation maps of FIGS. 6a-6c illustrate two conclusions reached by the present inventors. One is that a combination of the estimates of two attenuation coefficient estimation methods is generally more accurate than a single method alone. The other is that the accuracy of attenuation coefficient estimates can vary between underestimation and overestimation with image depth. The latter characteristic can be illustrated by plotting attenuation estimates produced by various techniques from acoustic transmission through different tissues as a function of depth. For the plots of FIG. 7, $\alpha_1$ denotes acoustic attenuation coefficients estimated by the spectral intensity difference method, $\alpha_2$ denotes acoustic attenuation coefficient estimated by the spectral frequency shift method, and $\alpha_0$ is ground truth, the true acoustic attenuation value of the tissue under examination. Measurement bias is defined as $\alpha_1-\alpha_0$ or $\alpha_2-\alpha_0$; measurement delta between the two estimation methods is defined as $\alpha_1-\alpha_2$, the measurement average is $(\alpha_1+\alpha_2)/2$, and the averaged bias is $(\alpha_1+\alpha_2)/2-\alpha_0$.

Figure 7:
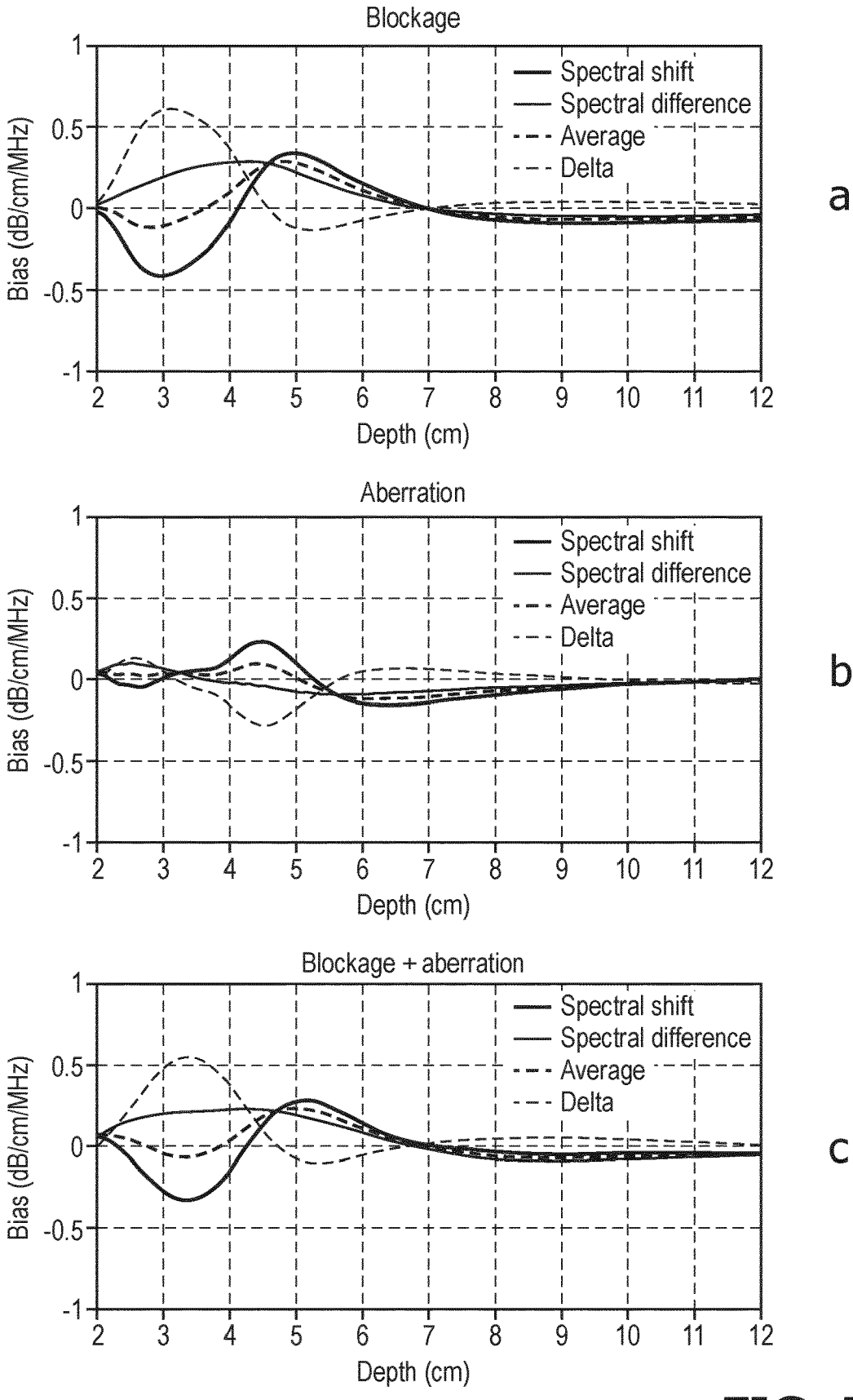
FIGS. 7a-7c illustrate three plots of attenuation coefficient bias for different estimation methods as a function of depth for three different acoustic path conditions.

The plots of FIG. 7 are for an array transducer operating with an azimuth focus at a depth of 4.8 cm, an elevation focus at a depth of 7 cm, and an elevation aperture reduction of 40%. The subject being measured is uniform liver tissue with an acoustic attenuation coefficient of 0.56 db/MHz/cm and a speed of sound (SOS) of 1540 m/sec. Overlying the liver tissue is a 2 cm fat layer with a lower SOS, thereby presenting an aberration problem. Each curve in FIG. 7 illustrates the variation of the attenuation measurement bias with reference to a nominal baseline of zero bias. FIG. 7a illustrates the effects of elevation aperture blockage. In FIG. 7a, the lowest curve at the 3 cm depth is the variation of bias when attenuation is estimated by the spectral shift method. This curve shows an underestimation of attenuation in the near field around 3 cm, changing to an overestimation around a depth of 5 cm. The method produces no bias at the elevation focal depth of 7 cm, and very little bias at deeper depths. The second curve down from the top at 3 cm is the variation of bias when attenuation is estimated by the spectral difference method. This curve shows overestimation in the near field peaking around 4.2 cm and dropping to zero bias at the elevation focal depth and remaining minimal thereafter. The second curve up from the bottom at 3 cm is the variation of the averaged bias, and shows an underestimation—overestimation—nominal curve, similar to the spectral shift method curve but with greater moderation. The uppermost curve at 3 cm is of the measurement delta of the two methods, which exhibits a significant overestimation in the near field followed by a small underestimation after the azimuth focal point, and no significant bias at the elevation focal point and thereafter. The different curves are seen to exhibit different patterns of overestimation and underestimation of the true attenuation at various depths in the image field.

The curves of FIG. 7b show the measurement bias caused by the aberration effects of the fatty layer. At the depth of 4.5 cm, the upper curve is for the spectral frequency shift method, the second curve down is the averaged bias, the third curve down is for the spectral difference method, and the bottom curve is the measurement delta curve. These curves show that the bias for all measurements is greatest in the vicinity of the azimuth focal depth of 4.8 cm. Otherwise, the measurement bias due to aberration effects is much less than that due to elevation aperture blockage.

FIG. 7c shows measurement bias curves for the combined effects of both aperture blockage and aberration. As a comparison of FIG. 7a with FIG. 7c shows, the combined effect curves are heavily dominated by and closely follow the patterns of the aperture blockage curves. Thus it may be concluded that elevation aperture blockage is the major source of attenuation measurement bias and that effects from aberration are negligible. It was also found that the azimuth focal position is less significant than the elevation focal position for the development of measurement bias. It was also found that more aperture blockage introduces higher measurement bias. As for the different methods of attenuation coefficient estimation, the spectral intensity difference method introduces mainly over-estimation in $\alpha_1$ in the pre-focal region of the elevation focal point and then slight underestimation in the post-focal region. In contrast, the spectral frequency shift method initially produces underestimation in $\alpha_2$ followed by overestimation in the pre-focal region. The curve then crosses zero again at the focal point and continues with slight underestimation in the post-focal region.

From the foregoing, the present inventors have developed a process for evaluating a number of criteria which are indicative of elevation aperture blockage. First, a metric which is developed from multiple attenuation coefficient estimation methods is used, such as the average of the estimation by the two methods $((\alpha_1+\alpha_2)/2)$, the absolute difference metric, or the relative difference metric as defined above. Second, tissue homogeneity is assessed. A process of the present invention is most effective when the tissue under examination is free of major ducts and blood vessels, a condition which underpins the accuracy of the spectral intensity difference method. Following these preliminary steps, an elevation blockage is detected when multiple ones of the following criteria are met (focal zones are with reference to the elevation focus of the transducer):

1) The average (or peak) measurement bias in the near field for the chosen metric is greater than $T_1$, where $T_1$ is a positive threshold. The threshold value $T_1$ is empirically determined; for the absolute difference metric a threshold of 0.3 dB/MHz/cm has been found to be suitable. Other metrics will have their own corresponding $T_1$ thresholds.

2) The average measurement bias in the far field peri- and post-focal zone is less than a positive threshold $T_2$. Again, the $T_2$ threshold is empirically determined and different metrics will have their own threshold values; a suitable $T_2$ threshold value for the absolute difference metric is 0.1 dB/MHz/cm.

3) The delta curve (see FIG. 7c, top curve at 3 cm) exhibits one or two zero-crossing points in the perifocal zone.

4) A low confidence factor score exists in the pre-focal zone.

While the foregoing criteria, when met, are all generally indicative of aperture blockage, identification of elevation aperture blockage using multiple ones of the criteria is more effective, and the technique is most robust when all four criteria are used.

Figure 8A:
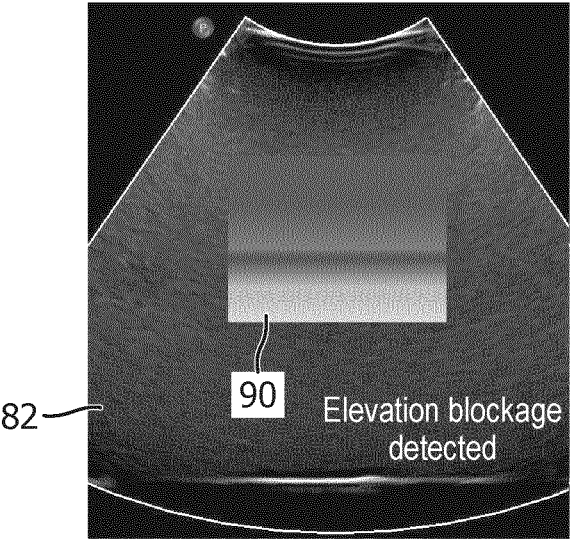
FIG. 8a illustrates an ultrasound image with a confidence map overlaying a region of interest and an alert that elevation blockage has been detected.
Figure 8B:
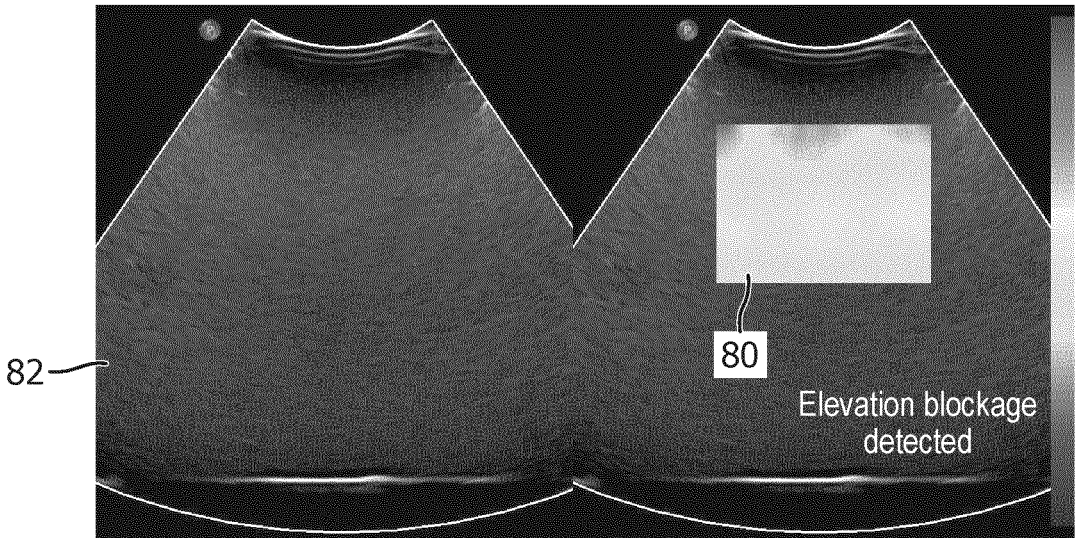
FIG. 8b illustrates a B mode image with an attenuation coefficient map overlaying a region of interest and an alert that elevation blockage has been detected.

Once the presence of elevation aperture blockage has been identified, the user is notified of the determination. FIG. 8a illustrates a B mode image 82 with a confidence factor map 90 superimposed over an ROI in the image. The darker shading in the upper (near field) portion of the confidence map indicates a low confidence score for the attenuation coefficient estimations in that portion. Below the confidence map is a user alert notifying the sonographer that "Elevation Blockage Detected". FIG. 8b similarly shows a B mode image with a superimposed attenuation coefficient map 80 and the "Elevation Blockage Detected" alert. An audio alert may additionally or alternatively be used.

In addition to notifying the sonographer of the elevation aperture blockage problem with an alert, it is also possible to provide guidance on ways to reduce or minimize the blockage. For instance, a message could be presented to the sonographer, suggesting that more pressure be applied to the transducer and to orient the transducer more parallel to the intercostal space. Another message could suggest adjustment of the patient pose. The patient in a liver exam could be asked to further extend the right arm and raise it above the head, or to take a left lateral decubitus position if currently in a supine position. Another message could suggest changing the acoustic window from an intercostal to a subcostal approach. Yet a further message could suggest using a different abdominal transducer with a smaller footprint. This is particularly helpful for pediatric patients and adult patients with narrow intercostal spaces.

Figure 9:
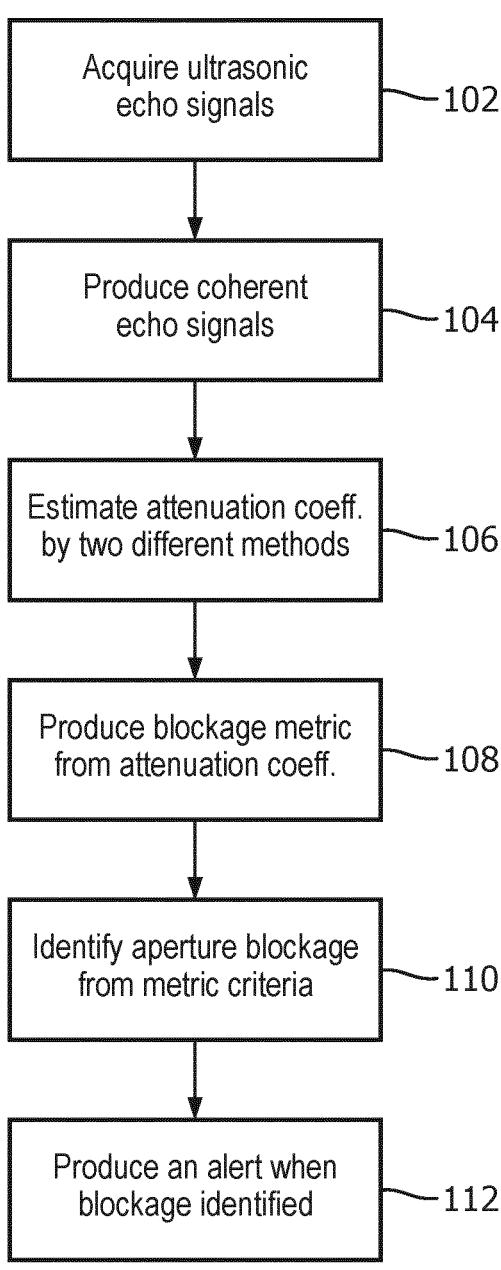
FIG. 9 is a flowchart of a method for detecting elevation aperture blockage in accordance with the principles of the present invention.

FIG. 9 is a flowchart of a method for detecting elevation aperture blockage in accordance with the present invention. In step 102, and ultrasound probe is used to acquire ultrasonic echo signals from an image field. In step 104 the echo signals are processed as by beamforming to produce coherent echo signals. In step 106 acoustic attenuation coefficient values are estimated by two different methods, such as the spectral frequency shift method and the spectral intensity difference method. In step 108 a blockage metric is produced from attenuation coefficient values. The metric may be based on an average, absolute difference, or relative difference of acoustic attenuation coefficients estimated by the two different methods, for instance. In step 110 criteria involving the metric such as overestimation or underestimation of attenuation measurement bias are examined to identify the presence of elevation aperture blockage. In step 112 an alert is produced when elevation aperture blockage is identified.

It should be noted that an ultrasound system suitable for use in an implementation of the present invention, and in particular the component structure of the ultrasound system of FIG. 1, may be implemented in hardware, software or a combination thereof. The various embodiments and/or components of an ultrasound system and its controller, or components and controllers therein, also may be implemented as part of one or more computers or microprocessors. The computer or processor may include a computing device, an input device, a display unit and an interface, for example, for accessing the internet. The computer or processor may include a microprocessor. The microprocessor may be connected to a communication bus, for example, to access a PACS system or the data network for importing training images. The computer or processor may also include a memory. The memory devices such as the image data memory 30 may include Random Access Memory (RAM) and/or Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine. The set of instructions of an ultrasound system including those controlling the acquisition, processing, and display of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. The equations given above for the different methods for attenuation coefficient estimation and mapping, as well as the calculations used to produce the confidence maps described above, are typically calculated by or under the direction of software routines. Further, the software may be in the form of a collection of separate programs or modules such as an attenuation coefficient computing module, or an attenuation coefficient mapping program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasonic diagnostic imaging system which produces attenuation coefficient maps of an image field comprising:

an ultrasound probe having a transducer array adapted to acquire ultrasonic echo signals from an image field;

a beamformer adapted to process the ultrasonic echo signals to produce coherent echo signals for an ultrasound image of the image field;

an attenuation coefficient processor, coupled to the beamformer, and adapted to estimate attenuation coefficient values for maps of attenuation coefficients;

an elevation blockage detector processor, coupled to the attenuation coefficient processor, and adapted to produce a metric developed from estimates of attenuation coefficients produced by two different estimation methods, wherein the elevation blockage detector processor is further adapted to identify the presence of elevation aperture blockage when one or more criteria based on the metric are satisfied; and wherein the system is further adapted to produce an alert in response to the identification of the presence of elevation aperture blockage.

2. The ultrasonic diagnostic imaging system of claim 1, wherein the metric is based upon attenuation coefficient measurement bias.

3. The ultrasonic diagnostic imaging system of claim 1, wherein the metric is based upon the average, the absolute difference, or the relative difference of acoustic attenuation coefficients estimated by the two different estimation methods.

4. The ultrasonic diagnostic imaging system of claim 1, wherein the two different estimation methods further comprise a spectral frequency shift method and a spectral intensity difference method.

5. The ultrasonic diagnostic imaging system of claim 2, wherein the criteria further comprise an evaluation of the metric as a function of depth.

6. The ultrasonic diagnostic imaging system of claim 5, wherein the criteria further comprise an evaluation of overestimation or underestimation of the estimated attenuation coefficient values as a function of depth.

7. The ultrasonic diagnostic imaging system of claim 1, wherein the system is further adapted to provide guidance on how to reduce or minimize the blockage.

8. The ultrasonic diagnostic imaging system of claim 1, further comprising a confidence processor adapted to produce confidence factor values; and a mapping processor adapted to produce a map of confidence factor values for attenuation coefficients.

9. The ultrasonic diagnostic imaging system of claim 8, further comprising:

a display adapted to produce an ultrasound image with the map of confidence factor values superimposed thereon.

10. The ultrasonic diagnostic imaging system of claim 9, wherein the display is further adapted to display the alert concurrently with a display of the superimposed confidence map.

11. The ultrasonic diagnostic imaging system of claim 9, wherein the display is further adapted to display the alert concurrently with a display of an attenuation coefficient map.

12. The ultrasonic diagnostic imaging system of claim 5, wherein the criteria vary as a function of depth.

13. The ultrasonic diagnostic imaging system of claim 5, wherein the criteria further comprise a confidence factor.

14. The ultrasonic diagnostic imaging system of claim 5, wherein the criteria further comprise an assessment of tissue homogeneity.

15. The ultrasonic diagnostic imaging system of claim 1, wherein one of the criteria is based on a number of zero crossings with depth of a curve of measurement difference between the two different estimation methods.

16. A method of detecting elevation aperture blockage during acoustic attenuation coefficient mapping with an ultrasonic diagnostic imaging system comprising:

operating an ultrasound probe to acquire ultrasonic echo signals from an image field;

producing coherent echo signals from the echo signals;

estimating attenuation coefficient values by two different attenuation coefficient estimation methods;

producing a blockage metric from estimated values of attenuation coefficients;

identifying elevation aperture blockage from criteria of the blockage metric; and producing an alert when an elevation aperture blockage is identified.

17. The method of claim 16 wherein estimating attenuation coefficient values by two different attenuation coefficient estimation methods further comprises estimating attenuation coefficient values by the spectral frequency shift method and by the spectral intensity difference method.

18. The method of claim 17, wherein producing a blockage metric from estimated values of attenuation coefficients further comprises producing a metric based upon the average, the absolute difference, or the relative difference of acoustic attenuation coefficients estimated by the two different estimation methods.

* * * * *